United States Patent [19]

Ripka

[11] 4,379,845

[45] Apr. 12, 1983

[54] YEAST PROCESS AND PRODUCT

[75] Inventor: Michael S. Ripka, Huntington, Conn.

[73] Assignee: Nabisco Brands, Inc., Parsippany, N.J.

[21] Appl. No.: 286,111

[22] Filed: Jul. 23, 1981

[51] Int. Cl.$^3$ .......................... C12N 1/16; C12N 1/18
[52] U.S. Cl. .................................. 435/255; 435/256;
435/800; 435/942; 426/60
[58] Field of Search ............... 435/255, 256, 261, 800,
435/942; 426/60; 127/54; 210/637, 651

[56] References Cited

U.S. PATENT DOCUMENTS

| | | | |
|---|---|---|---|
| 1,687,561 | 10/1928 | Hoffman et al. | 435/255 X |
| 1,860,832 | 5/1932 | Bennett et al. | 435/255 |
| 2,075,127 | 3/1937 | Mead, Jr. | 435/255 |
| 3,974,068 | 8/1976 | Ebner et al. | 210/637 |
| 3,982,024 | 9/1976 | Oneto | 426/15 |
| 4,115,147 | 9/1978 | Shimizu et al. | 210/651 X |
| 4,192,918 | 3/1980 | Stineman et al. | 435/942 X |
| 4,237,232 | 12/1980 | Yoshizawa et al. | 435/255 X |

FOREIGN PATENT DOCUMENTS 1184514  3/1970  United Kingdom ................ 435/311

*Primary Examiner*—Robert A. Yoncoskie
*Attorney, Agent, or Firm*—Richard Kornutik

[57] ABSTRACT

Disclosed are an improved process for preparing yeast from molasses. In its preferred aspects, final molasses is adjusted to a density of from about 20° to about 40° brix, desludged, passed through an ultrafiltration device effective to reject molecules having molecular weights greater than about 30,000 daltons to produce a first permeate, and passed through at least one additional filtration device having an average pore diameter within the range of from about 0.2 to about 0.5 microns to produce a yeast culture medium. The filtration steps are effective in combination to reduce the microorganism count to a level effective to produce yeast suitable for food use; preferably, less than 1 organism per gram of medium. Bakers' yeast are propagated in the medium in increased yield of yeast per unit weight of molasses solids. Additionally, the activity, color and odor of the yeast are improved, while the energy requirements for the process and the BOD and COD loading for the process effluent are decreased.

9 Claims, 1 Drawing Figure

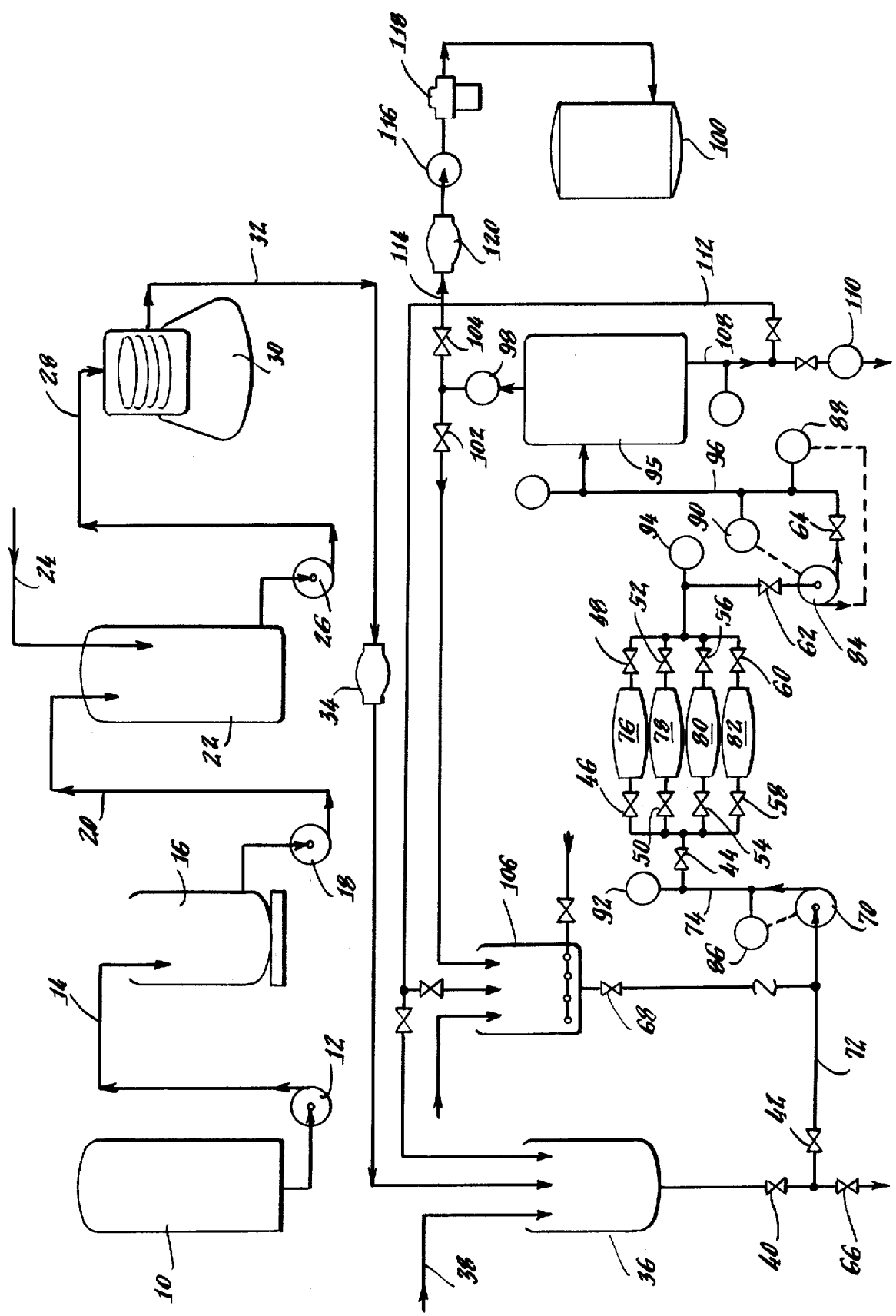

YEAST PROCESS AND PRODUCT

BACKGROUND OF THE INVENTION

The present invention relates to an improved process for preparing yeast. More particularly, it relates to a process which produces yeast in improved yields and of improved quality.

Commercial yeast production typically entails propagation in a plurality of stages. Generally, yeast are innoculated into a presterilized nutrient medium usually contained in a shaker flask. In the flask, growth of the yeast is encouraged by various means such as controlling the temperature and shaking the flask to effect aeration. The yeast are removed from this flask and innoculated into another flask containing a larger volume of nutrient medium for continued growth. These initial stages may conveniently be referred to as flask or culture development stages.

From the culture development stages, the yeast may be innoculated into a vessel having an air source and means of agitation. These steps may be repeated once or twice using greater amounts of nutrient medium and larger vessels. Because the amount of air used in these stages is generally restricted, these stages are commonly referred to as slightly aerobic stages. Yeast from these stages are then transferred into larger fermentors where vigorous growth conditions are maintained, including the use of large volumes of air. These stages may be referred to as highly aerobic, or commercial, stages since the yeast from these stages are harvested and processed for bakery or home use, typically in compressed or active dry form.

For propagation in the highly aerobic or commercial stages, it is necessary to prepare large quantities of a yeast culture medium which is substantially free of microorganisms. This has been accomplished in the past by sterilizing the medium such as final molasses, by heat treatment. To reduce the microorganism count to a level effective to produce yeast suitable for food use, large amounts of energy, as well as means for generating and transferring heat to the process, were required. Typically, the heat was generated in oil or gas-fired boilers and transferred to the process as steam which could be injected live or transferred by means of heat exchangers. Thus, this sterilization step entailed sizable capital and operational costs. It would be desirable to reduce these costs.

Typically, the culture medium would contain molasses. Molasses is the thick liquid which is left after sucrose has been removed from the mother liquor in sugar manufacture from either beets or cane. Molasses does not have an absolutely fixed composition because of the many variations in commercial sugar production and the various stages in the process at which it may be withdrawn. Typically, however, a product known as "final molasses" contains about 20% sucrose, 20% reducing sugars, 10% ash, 20% non-sugar organic materials, and 20% water. This product is essentially the syrup which remains when it is no longer commercially practical to remove further sucrose. This product, also known as "black strap molasses" is typically utilized to produce yeast, vinegar, and various organic chemicals, such as alcohols, through fermentation.

In U.S. Pat. No. 4,101,338, to Rapaport et al, there is disclosed a process for fractionating carbohydrate-containing materials, such as molasses, which enables further extraction of sugars. According to that procedure, several fractions are obtained by contacting the material with an ion exchange resin. In one embodiment, ultrafiltration is employed to remove higher molecular weight color bodies from the molasses prior to fractionation. The process does not, however, utilize the decolorized molasses for production of yeast nor other known uses, but fractionates the molasses into a number of new products, each having independent utility and economic value.

In recent years, ultrafiltration membranes have been employed in a number of unit operations to remove bacteria, separate polysaccharides based on molecular weight, remove ash, and a number of other procedures. For example, U.S. Pat. No. 3,228,877 to Mahon, U.S. Pat. No. 3,419,144 to Huntington, U.S. Pat. No. 3,974,068 to Ebner et al and U.S. Pat. No. 3,982,024 to Oneto, all employ membranes to remove microorganisms from solutions. In addition to the discussion by Rapaport et al that color may be removed from carbohydrate-containing solutions, similar disclosures are found in U.S. Pat. No. 4,115,147 to Shimizu et al wherein a nutritive sugar is produced by a non-centrifugal process employing ultrafiltration, and in U.S. Pat. No. 4,211,577 to Wallin which teaches the extraction of anthocyanin colors from materials such as grape juice. In addition to color removal, Shimizu further teaches the removal of ash and high molecular weight components. Also relating to the removal of ash from raw sugar juice is U.S. Pat. No. 3,799,806 to Madsen. Among the many further disclosures which relate to the removal of high molecular weight components, are those of Rapaport and Shimizu mentioned above, and also U.S. Pat. No. 3,668,007 to Egger et al, U.S. Pat. No. 3,756,853 to Meyer, U.S. Pat. No. 3,832,285 to Kurimoto, and U.S. Pat. No. 4,069,103 to Muller. However, to the best of my knowledge, current commercial yeast production does not employ ultrafiltration to pretreat the molasses employed as the yeast culture medium. Moreover, the prior art does not anywhere suggest that yields of yeast based on the quantity of molasses employed, nor the leavening activity of the resulting yeast based on the effectiveness per weight of product yeast, could be improved by a process employing ultrafiltration.

SUMMARY OF THE INVENTION

It is an object of the present invention to provide a process for preparing yeast in improved yield.

It is another object of the present invention to provide a process for preparing yeast having improved leavening activity.

It is a further object of the present invention to provide a process which enables the production of yeast with decreased energy consumption.

It is yet another object of the present invention to provide a process for producing the yeast which decreases the BOD and COD loading of the process effluent.

It is still another object of the invention to provide a process for producing yeast with improved cosmetic properties such as color and odor.

These and other objects are accomplished according to the present invention which provides an improved process for preparing yeast and the product of that process. The method, in its broad aspects, comprises: purifying molasses by passing the molasses through an ultrafiltration device effective to reject solids having molecular weights greater than about 30,000 daltons to produce a first permeate, and passing the first permeate through at least one additional filtration device having an average pore diameter of from about 0.2 to about 1.2 microns to produce a yeast culture medium, where the filtration devices are effective in combination to reduce the microorganism count to a level effective to produce yeast suitable for food use; innoculating the yeast culture medium with yeast; and subjecting the yeast and the yeast culture medium to conditions effective to propagate the yeast.

BRIEF DESCRIPTION OF THE DRAWING

The invention will be better understood and its advantages will become more apparent from the following description, especially when read in light of the attached drawing, wherein:

the FIGURE is a schematic representation of a preferred processing system according to the present invention.

DETAILED DESCRIPTION

The process of the invention improves the production of yeast essentially by providing an improved process for purifying the molasses employed as the yeast culture medium. By the term molasses, it is meant not only final molasses, which has a relatively low economic value due to the high degree of depletion of sucrose, but to other forms of sugar liquors from which significant quantities of sucrose can be crystallized. For example, it is meant to include the mother liquor remaining after the first crystallization of sucrose, commonly referred to as "first molasses". Also included are "second molasses" which is the mother liquor obtained from the second crystallization, as well as each successive stages of molasses on through final molasses. It is also possible to employ whole juice molasses; however, this may not be economically desirable under many conditions.

Likewise, the term molasses is not restricted to molasses produced from any particular source, but can be the end product from a sugar cane or a sugar beet process. In its broad aspects, then, the molasses can be of any sucrose content or botanical source which provides an effective source of carbohydrate for the propagation of yeast.

The yeast culture medium may be comprised of the molasses alone or can employ further nutrients, salts and the like as may be necessary to obtain the proper amounts of nitrogen, phosphorous, carbohydrate, and minor nutrients as may be required by the particular strain of yeast or its desired end use. It may also be desirable to employ an acid or an alkali to adjust the pH to a suitable value, typically in the range of from about pH 3.5 to about pH 7.

The largest use for viable yeast is for baking purposes, and the process of the present invention is particularly suitable for preparing yeast of this type. Yeast are supplied to bakeries and to consumers for baking in two principal forms, i.e., active dry and compressed. The species of yeast used for baking purposes is generally *Saccharomyces Cerevisiae*. There are many strains of yeast which are included within the species and the particular strain used depends upon many factors, such as the desired form of the yeast.

Strains of bakers' yeast can be generally grouped into broad categories when classified according to the bios response procedure published by Shultz and Atkin in *ARCHIVES OF BIOCHEMISTRY*, Vol. 14, Page 369 (August 1947). The first group is classified as Bios No. 236. Yeast in this group are generally used when it is desired to produce compressed yeast. Compressed yeast are generally formed into bricks of suitable size and contain about 70% moisture. The second group is classified as Bios No. 23, and is typically employed when active dry yeast is to be produced. Although yeast of the Bios No. 23 group can be propagated to higher yields, and are hardier and more stable than yeast of the Bios No. 236 group, compressed yeast of the latter group are preferred by commercial bakers because of their superior leavening activity.

Active dry yeast typically contain less than 10% moisture, and generally from about 4 to 8% moisture. Yeast of the Bios No. 23 group are usually selected for the production of active dry yeast because the properties of yeast of this group, of being more hardy and metabotically stable than yeast of Bios No. 236, enables Bios group 23 yeast to be dried to lower moisture levels with minimum loss of initial leavening activity. In some instances, yeast of Bios No. 236 group can be used to prepare an active dry yeast product.

The FIGURE shows a preferred process scheme for carrying out the present invention. Raw molasses, as stored in tank 10, has a high bacterial count, typically on the order $10^7$ microorganisms per gram of liquid molasses, which must be reduced prior to propagation. This is necessary because the conditions for growing the yeast are also highly favorable for the growth of bacteria. It is also necessary to reduce the level of bacteria in all feed streams and process equipment to the lowest practical level. For example, the large air supply required for propagating the yeast under aerobic conditions must be filtered. Additionally, apparatus must be kept scrupulously clean and be sterilized on a regular basis. Similarly, the yeast itself must be obtained from cultures which are as free as possible from contaminating bacteria. The processing of the present invention will purify the raw molasses in a manner which will improve the overall production and quality of yeast.

The raw molasses held in 10 is transferred by means of a positive displacement pump 12, through line 14 to scale tank 16. The amount of molasses placed in tank 16 is determined either gravimetrically or volumetrically, and according to production requirements. A positive displacement pump 18 transfers molasses through line 20 to the dilution tank 22. Hot water added via line 24 is mixed with the raw molasses to give a solution of approximately from about 50° to about 70° brix, and a temperature of from about 120° to about 135° F. The diluted molasses is transferred by pump 26 through line 28 to the desludger 30, which is either a centrifugal or filter screen unit. The primary purpose of the desludger 30 is to remove particulate matter suspended in the molasses solution, and reject particles greater than about 90–100 microns. One particularly effective desludging unit is a 100 micron SWECO screen system.

Molasses passes from the desludger 30 through line 32 through mass flow meter 34 to the feed tank 36. Hot water added via line 38 is mixed with the diluted molasses to give a final concentration of from about 20° to about 50° brix at a temperature of from about 120° to about 130° F. Opening valves 40, 42, 44 through 60, 62 and 64, while holding closed valves 66 and 68, allows molasses to be pumped via pump 70 through lines 72 and 74 to protective filter/screens, of which there are four illustrated, 76 through 82. These protective filters or screens are rotary strainers.

Pump 84 moves molasses through the ultrafiltration system. Low pressure limit sensor 86 is used to protect pump 70. In a similar manner, pressure limit sensor-switch 88 protects pump 84. A high temperature sensor and limit switch 90 is installed to assure temperature protection to the ultrafiltration system downstream. Pressure indicators, 92 and 94, are used to monitor filter/screens 76 through 82 for fouling indications. The molasses is moved via line 96 through ultrafiltration system 95, which in one typical configuration contains about twenty spirally-wound units.

Permeate is passed through flow meter 98, whereafter it can be taken forward to permeate collection tank 100 by closing valve 102 and opening valve 104, or recycled to tank 106, by opening valve 102 and holding valve 104 closed. The recycle circuit is primarily used during cleaning of the equipment but can also be used to recover low density permeate generated by diafiltration. The concentrate is withdrawn from the ultrafiltration system through line 108. This concentrate can be drained through flow meter 110 or recycled via line 112 back to feed tank 36. This concentrate recycle circuit is primarily included for cleaning in place of the system, but can also be used to generate concentrate for diafiltration.

The ultrafiltration system 95 is shown in this exemplary situation as ABCOR Spiral-type membrane cartridges. To be effective according to the present invention, the ultrafiltration device must be capable of rejecting suspended and dissolved solids having molecular weights greater than 30,000 daltons. If desired, ultrafiltration devices which are capable of rejecting solids having molecular weights as low as 10,000 daltons can be employed. Preferably, the device should be capable of rejecting solids having molecular weights above a minimum level of from about 15,000 to about 20,000 daltons.

Permeate is moved through line 114 to pump 116 through at least one polishing filter 118, in this case shown as a membrane cartridge system, to a permeate holding tank 100. The membrane cartridge system 118 will preferably have a prefilter followed by one or more membrane filters. This filtration device 118 is required for commercial utility to reduce the microorganism count to an effectively low level where permeates may stand for up to five days after preparation. These filters are effective to remove substantially all remaining microorganisms. The membrane filters will have average pore diameters of from about 0.2 to about 1.2, preferably from 0.2 to 0.5, microns. The permeate passed through this membrane cartridge system is the yeast culture medium which will be employed in the propagation of yeast. The filter 118 is effective to reduce the microorganism count of the molasses to a level suitable for the production of yeast. Preferably, the microorganism count is reduced to less than 1 microorganism per gram of yeast culture medium.

Among the preferred membrane cartridge devices employable at this stage in the process are Millipore CVGL and/or CVHL filters. Preferably, those having an average pore diameter of about 0.2 to about 0.5 microns are employed. In one exemplary situation, one in-line prefilter, such as a Millipore CWSC, is employed in conjunction with another membrane cartridge device, such as a final T cartridge-type filter, such as a Millipore CVGL characterized by the manufacturer as polymeric membrane having a pore diameter of 0.2 to 0.5 microns. The exact type of filter employed according to the present invention is not presently believed critical so long as it is sterilizable by steam in place, is non-wettable, has an acceptable pressure drop, and is effective to provide the desired degree of microorganism reduction.

The yeast culture medium is withdrawn from permeate tank 100 and can be passed, if desired, through yet another membrane cartridge filter, which can be of the type employed for cartridge system 118. This may be desirable where the permeate is held for extended periods of time prior to use as the yeast culture medium, wherein any bacteria present would propagate.

Preferably, a flow meter (not shown) is employed to meter the flow of yeast culture medium to a culturing tank (not shown). Mass balance through the ultrafiltration system as a whole is facilitated using mass flow meters, 34 and 120. Meter 34 is mounted in line 32 and measures total molasses feed to feed tank 36. Mass flow meter 120 is mounted in line 114 and measures total permeate withdrawn. The actual culturing of the yeast is well known and understood in the art, and is described, for example, by Frederick W. Nordsiek in *FOOD ENGINEERING*, McGraw Hill Publishing Company, New York, N.Y., May 1951. Also descriptive are U.S. Pat. No. 3,617,306 to Seymour Pomper and U.S. Pat. No. 4,008,335 to Immanuel Akerman and Seymour Pomper. After culturing for the desired period of time and at the effective temperatures, the suspension of yeast cells in the yeast culture medium is withdrawn and passed to a separator device of known construction. The separator device separates the cream yeast while extracting the beer.

The following example is presented for the purpose of further illustrating and explaining the present invention and is not be taken as limiting in any regard. Unless otherwise indicated, all parts and percentages are by weight.

EXAMPLE

According to this example, two batches of yeast are cultured employing molasses purified in accordance with the preferred processing conditions described in connection with the attached FIGURE. These batches of yeast are compared to a control which averages one month of commercial production of the same type of yeast from the same type of molasses wherein the yeast culture medium is sterilized by heating to a temperature of about 142° C. with steam after desludging instead of the use of filtration according to the present invention. The molasses employed in the preparation of the control samples is diluted typically to within a range of from about 55° to about 65° brix.

The preparation of the test and control batches of yeast and the characteristics of the resulting products are summarized in the following table below:

TABLE I

|  | Invention Run A | Invention Run B | Control |
|---|---|---|---|
| Mash Size (pounds) | 4,000 | 4,000 | 14,000 |
| Molasses (weight ratio) | 80 beet/20 cane | 80 beet/20 cane | 80 beet/20 cane |
| (weight, pounds) | 3,270 | 3,340 | 14,000 |
| Permeate (volume, gals) | 1,190 | 1,104 | — |
| Sugar (%) | 13.0–13.5 | 14.6 | — |
| Stock Yeast (pounds) | 1200 | 1300 | 4200 |
| Gross Yield @ 70% (pounds) | 4200 | 4400 | 14,115 |
| Net Yield (pounds) | 3000 | 3100 | 9,915 |
| Yield, Molasses | | | |

TABLE I-continued

|  | Invention Run A | Invention Run B | Control |
|---|---|---|---|
| basis (%) | 91.7 | 92.8 | 70.8 |
| Protein (%) | 36.1 | 41.8 | 41.0 |
| Phosphate (%) | 1.70 | 1.90 | 1.99 |
| Leavening-Straight Dough (cc) | 143 | 153 | 140 |
| Leavening-High Sugar (cc) | 113 | 121 | 113 |

The above description is for the purpose of teaching the person of ordinary skill in the art how to practice the present invention and is not intended to detail all of its obvious modifications and variations which will become apparent to the skilled worker upon reading. It is intended, however, to include all such modifications and variations within the scope of the present invention which is defined by the following claims.

What is claimed is:

1. An improved process for culturing yeast which comprises: purifying molasses by passing the molasses through an ultrafiltration device effective to reject solids having molecular weights greater than about 30,000 daltons to produce a first permeate, and passing the first permeate through at least one additional filtration device having an average pore diameter of from about 0.2 to about 1.2 microns to produce a yeast culture medium, wherein the filtration devices are effective in combination to reduce the microorganism count to a level effective to produce yeast suitable for food use; innoculating the yeast culture medium with yeast; and subjecting the yeast and yeast culture medium to conditions effective to propagate the yeast.

2. A process according to claim 1 wherein the yeast comprises bakers' yeast.

3. A process according to claim 1 wherein the microorganism count is reduced to less than 10 microorganisms per gram of yeast culture medium.

4. A process according to claim 3 wherein the microorganism count is reduced to about 1 or less microorganism per gram of yeast culture medium.

5. A process according to claim 1 wherein said ultrafiltration device is effective to reject suspended solids having molecular weights greater than about 15,000 daltons.

6. A process according to claim 1 wherein the additional filtration device comprises a membrane filter having an average pore diameter of from about 0.2 to about 0.5 microns.

7. A process according to claim 1 wherein the process of purifying the molasses includes desludging in a screen-type unit.

8. A process according to claim 1 wherein the process of purifying the molasses includes desludging in a centrifugal-type unit.

9. A process according to claim 1 wherein the density of the molasses is adjusted by the addition of water to a density of from about 20° to about 40° brix prior to passing the molasses through said ultrafiltration device.

* * * * *